United States Patent
Schulz (10) Patent No.: US 9,976,999 B2
(45) Date of Patent: May 22, 2018

(54) METHOD AND DEVICE FOR CARRYING OUT THIN-LAYER CHROMATOGRAPHY

(71) Applicant: MERCK PATENT GMBH, Darmstadt (DE)

(72) Inventor: Michael Schulz, Darmstadt (DE)

(73) Assignee: MERCK PATENT GMBH, Darmstadt (GB)

(*) Notice: Subject to any disclaimer, the term of this patent is extended or adjusted under 35 U.S.C. 154(b) by 259 days.

(21) Appl. No.: 14/654,018

(22) PCT Filed: Nov. 25, 2013

(86) PCT No.: PCT/EP2013/003553
§ 371 (c)(1),
(2) Date: Jun. 19, 2015

(87) PCT Pub. No.: WO2014/094958
PCT Pub. Date: Jun. 26, 2014

(65) Prior Publication Data
US 2015/0355149 A1    Dec. 10, 2015

(30) Foreign Application Priority Data
Dec. 20, 2012 (EP) .................... 12008479

(51) Int. Cl.
*G01N 30/91* (2006.01)
*B01D 15/08* (2006.01)
(Continued)

(52) U.S. Cl.
CPC ............ *G01N 30/91* (2013.01); *B01D 15/08* (2013.01); *G01N 35/10* (2013.01); *B01L 3/0293* (2013.01); *G01N 2030/027* (2013.01)

(58) Field of Classification Search
CPC .. G01N 30/91; G01N 35/10; G01N 2030/027; B01D 15/08; B01L 3/0293
(Continued)

(56) References Cited

U.S. PATENT DOCUMENTS 3,904,372 A    9/1975   Lightner
4,161,508 A *  7/1979   Janchen ........... G01N 27/44743
                                                  222/160

(Continued)

FOREIGN PATENT DOCUMENTS

| CH | 692008 A5 | 12/2001 |
| DE | 2401382 A1 | 7/1974 |
| DE | 2818576 A1 | 10/1979 |

OTHER PUBLICATIONS

Robotic work station for microscale synthetic chemistry: On-line absorption spectroscopy, quantitative automated thin-layer chromatography, and multiple reactions in parallel; by Lindsey et al., Rev. Sci. Instrum. 59 (6), Jun. 1988, p. 940-950.*

(Continued)

*Primary Examiner* — Manish S Shah
*Assistant Examiner* — Suman K Nath
(74) *Attorney, Agent, or Firm* — Millen, White, Zelano & Branigan, P.C.; William Nixon (57) ABSTRACT

A method for performing thin-layer chromatography applies a liquid sample to a separating layer. A mobile phase is subsequently applied to the separating layer and brought into contact with the liquid sample. After a developmental phase, a thin-layer chromatogram is produced. The liquid sample is taken up from a sample storage container with the aid of an autopipette using a new pipette tip for each sample application operation and applied to the separating layer. A device for performing the method includes a support plate for the accommodation of the separating layer, a first storage con- (Continued)

tainer for the accommodation of the sample, and a second storage container for the accommodation of the mobile phase.

12 Claims, 3 Drawing Sheets

(51) Int. Cl.
    *G01N 35/10*     (2006.01)
    *G01N 30/02*     (2006.01)
    *B01L 3/02*     (2006.01)

(58) Field of Classification Search
    USPC .......... 73/61.52, 61.55, 61.54; 422/509, 501, 422/525
    See application file for complete search history.

(56) References Cited

U.S. PATENT DOCUMENTS

| | | | |
|---|---|---|---|
| 5,811,665 A * | 9/1998 | Gregor | B01D 15/22 210/198.2 |
| 9,063,047 B2 * | 6/2015 | Van Berkel | G01N 1/4055 |
| 9,465,017 B2 * | 10/2016 | Loppacher | G01N 30/90 |
| 2011/0089096 A1 * | 4/2011 | Linford | B01J 20/28007 210/198.3 |
| 2011/0284735 A1 | 11/2011 | Van Berkel et al. | |
| 2012/0125127 A1 | 5/2012 | Loppacher et al. | |

OTHER PUBLICATIONS

Automating combinatorial chemistry: A primer on benchtop robotic devices; by Hardin et al., Molecular Diversity, I (1995) 270-274.*
International Search Report dated Feb. 28, 2014 issued in corresponding PCT/EP2013/003553 application (pp. 1-8).
Lindsey, et al., "Robotic Work Station for Microscale Synthetic Chemistry: On-Line Absorption Spectroscopy, Quantitative Automated Thin-Layer Chromatography, and Multiple Reactions in Parallel", Review of Scientific Instruments, vol. 59, No. 6 (Jun. 1988) pp. 940-950.
Hardin, et al., "Automating Combinatorial Chemistry: A Primer on Benchtop Robotic Systems", Molecular Diversity, vol. 1 (Aug. 1996) pp. 270-274.
Ford, et al., "An improved thin-layer chromatography/mass spectrometry coupling using a surface sampling probe electrospray ion trap system", Rapid Communications in Mass Spectrometry, vol. 18, No. 12 (Jun. 2004) pp. 1303-1309.
Van Berkel, et al., "Application of a Liquid Extraction Based Sealing Surface Sampling Probe for Mass Spectrometric Analysis of Dried Blood Spots and Mouse Whole-Body Thin Tissue Sections", Analytical Chemistry, vol. 81, No. 21 (Oct. 2009) pp. 9146-9152.

* cited by examiner

METHOD AND DEVICE FOR CARRYING OUT THIN-LAYER CHROMATOGRAPHY

FIELD OF THE INVENTION

The invention relates to a device and a method for carrying out thin-layer chromatography in which a liquid sample is applied to a separating layer, in which a mobile phase is subsequently applied to the separating layer and brought into contact with the sample, and in which, after a development phase, a thin-layer chromatogram is produced and can be evaluated.

DESCRIPTION OF THE RELATED ART

Thin-layer chromatography has been employed and used for many years for the analysis of sample substances. A mobile phase moves along a solid, fine-pored support material of a separating layer owing to capillary forces, and various sample substances are carried along by the mobile phase at different speeds or efficiencies, and the distance moved by a component of the sample within a prespecified development duration is characteristic of the component in question, so that the composition of the sample can be determined from a spatial evaluation of the distribution of the sample substances after the development phase.

Thin-layer chromatography is extensively employed in many areas of application for the analysis of unknown samples. In order to simplify the performance of thin-layer chromatography, various approaches are known for automating individual method stages of thin-layer chromatography. DE 2 401 382, for example, discloses that the sample can be applied in an automated manner to a separating layer with the aid of a capillary. The capillary must be cleaned after each application operation in order to prevent contamination of a fresh sample with residues of earlier samples.

Further developments are known from practice by means of which individual method steps that are necessary for carrying out thin-layer chromatography can be automated.

CH 692 008 A5 describes a method in which a liquid sample and a mobile phase can be sprayed onto a separating layer. The requisite device for carrying out thin-layer chromatography has an application device which can be moved in a plane for the automated application of a sample and a mobile phase to a separating layer which is necessary and used for development. In this method, a liquid jet, by means of which either a sample or the mobile phase can be sprayed onto the separating layer, is discharged from a print head. It is likewise necessary in the case of this device to clean the print head after each application operation. Otherwise, residues of an earlier application operation remaining in the print head may cause various samples, or various thin-layer chromatograms, to be contaminated by sample substance residues or mobile phase residues and prevent them from being evaluated in a meaningful manner. Although the performance of thin-layer chromatography can be automated by a device of this type, rapid performance of thin-layer chromatography is hindered by numerous cleaning operations which are absolutely necessary between individual automated application operations for the sample or for the mobile phase.

There are currently no known methods or devices which enable automated and rapid performance of a plurality of thin-layer chromatography operations and at the same time ensure that contamination of individual measurements by contamination with residues of preceding measurements or measurements carried out in parallel can be excluded.

SUMMARY OF THE INVENTION

It is therefore regarded as an object of the present invention to improve the known methods for thin-layer chromatography in such a way that thin-layer chromatography can be carried out and evaluated as rapidly as possible and in a substantially automated manner.

This object is achieved in accordance with the invention by the liquid sample being taken up from a sample storage container with the aid of an autopipette using a new pipette tip for each sample application operation and applied to the separating layer. The pipette tip used for a sample application operation can be separated from the autopipette after each application operation, removed and disposed of. This basically enabled the exclusion of contamination of subsequent sample application operations by residues of a sample which was applied to the separating layer during a preceding application operation.

The present invention therefore relates to a method for carrying out thin-layer chromatography in which one or more liquid samples are applied to a separating layer (14), in which a mobile phase is subsequently applied to the separating layer (14) and brought into contact with the sample, and in which, after a development phase, a thin-layer chromatogram is produced, characterised in that the one or more liquid samples are taken up from one or more sample storage containers (11, 12, 13) with the aid of an autopipette (4) using a new pipette tip (8, 9) for each sample application operation and applied to the separating layer (14).

The same sample can be applied one or more times from one storage container and/or two or more different samples can be applied from different sample storage containers.

In an embodiment of the method according to the invention, the mobile phase is taken up from a mobile phase storage container (16) using a new pipette tip (8, 9) for each mobile phase application operation and applied to the separating layer (14).

In an embodiment, a mobile phase storage container (16) filled with mobile phase is connected to the separating layer (14) via a contact device (22) comprising a capillary-active material.

In an embodiment of the method according to the invention, an eluent is taken up using a new pipette tip (8, 9) for each elution and brought into contact with an area of the separating layer (14) to be evaluated, and the eluate is fed to an evaluation device (20). The feed to the evaluation device is preferably carried out by taking up the eluate in the pipette tip again and feeding it to the evaluation device using the latter.

In another embodiment, an area of the separating layer (14) to be evaluated is stamped out using a new pipette tip (8, 9) for each separation operation and fed to an evaluation device (20).

In another embodiment, an area of the separating layer (14) to be evaluated is sealed off as far as the base support using a new pipette tip (8, 9) for each elution, the sorbent located in the sealed-off area is brought into contact with an eluent, and the eluate formed is taken up in the pipette tip again and fed to an evaluation device (20).

The present invention also relates to a device (5) for the automated performance of thin-layer chromatography, having a support plate (15) for the accommodation of a separating layer (14), at least having a first storage container (10,

11, 12, 13) for the accommodation of a sample and having a second storage container (16) for the accommodation of a mobile phase, characterised in that the device (5) has an automatic pipetting device (4) which can be moved over one surface of the support plate (15) and over the first storage container (10, 11, 12, 13) and the second storage container (16) and has a stock of pipette tips (8, 9), which can be taken up successively by the pipetting device (4), used and subsequently detached from the pipetting device (4) again and removed.

In an embodiment, the support plate (15) is arranged in a movable manner in a housing of the device (5).

In an embodiment, the support plate (15) can be connected to the storage container (16) for the mobile phase via a contact device (22) comprising a capillary-active material.

In an embodiment, the device (5) has a development container for the accommodation of the support plate (15). This development container is typically essentially closed, so that constant ambient conditions are ensured during the development.

In an embodiment, at least two different types of pipette tips (8, 9) are stored in a storage container (7) for pipette tips (8, 9).

In a preferred embodiment, the device (5) has a storage container (21) for an eluent.

In an embodiment, the device (5) has pipette tips (8, 9) for separating out an area of the separating layer (14) and for transfer of the separated-out area of the separating layer (14) to an evaluation unit (20).

In an embodiment, the device (5) has pipette tips (8, 9) for sealing off a sorbent area of the separating layer (14) from the base support, elution of the sorbent area with eluent and for transfer of the eluate to an evaluation unit (20).

In accordance with the invention, a separating layer consists of a base support to which a sorbent layer is applied. Separating layers for thin-layer chromatography, also called TL (thin-layer) plates, are known to the person skilled in the art. Sorbent layers comprising silica gel or silica gel derivatised with functional groups, such as amino groups or alkyl groups, or also underivatised or derivatised aluminium oxide, magnesium silicate, kieselguhr, polyamide or cellulose are typically applied here to a base support comprising glass, plastic or aluminium.

Mobile phases for thin-layer chromatography are known to the person skilled in the art. The person skilled in the art will be able to find a suitable mobile phase for the separating layer and the sample to be analysed.

In accordance with the invention, an application operation may comprise one or more pipetting operations, where in each case only liquid is removed from one storage container. Preferably, pipetting is only carried out once per application operation. However, it is also possible, for example in the case of filling of a storage container for the accommodation of a mobile phase which is connected to the separating layer via a contact device comprising a capillary-active material, for double or multiple pipetting to be necessary in order to produce an adequate fill depth of the storage container. In this case, double or multiple pipetting using the same pipette tip can be carried out in one application operation.

In accordance with the invention, samples are liquids whose composition is to be investigated by thin-layer chromatography. These liquids typically comprise one or more components or sample substances dissolved therein.

Various pipette tips which are suitable for once-only or short-term use with the autopipette are available commercially and inexpensively. For the application of the samples, use is typically made of pipette tips for the pipetting of sample volumes between 0.1 and 10 µl, for example pipette tips for the pipetting of 0.1 to 2 µl, of 1 to 5 µl or of up to 10 µl, depending on the concentration of the sample substances present in the sample. For the pipetting of the mobile phase, use is typically made of pipette tips which are suitable for liquid volumes between 100 µl and 1 ml.

In the case of elution, pipette tips for volumes between 10 and 100 µl are typically employed.

It has been found that sufficiently accurate and precise dispensing and application of the sample to the separating layer is possible using an autopipette in combination with suitable pipette tips.

A mobile phase can subsequently be applied to the separating layer and the chromatogram developed.

In an embodiment, it is provided that the mobile phase is taken up from a mobile phase storage container using a new pipette tip for each mobile phase application operation and applied to the separating layer. The autopipette here can advantageously be used not only for the application of the sample, but also for the application of the mobile phase directly to the separating layer. The different amounts in each case and the positioning accuracy of the various substances can be supported and accelerated by a suitable choice of pipette tips. If the mobile phase is pipetted directly onto the separating layer, circular chromatograms are typically developed. To this end, the mobile phase is, in an embodiment, pipetted directly onto the sample spot applied previously. Capillary forces cause the formation of a circular mobile phase front, and the sample is transported outwards in a circular manner. Alternatively, a plurality of samples can be applied in a circle to the separating layer. The mobile phase is then applied in the centre of the circle and forms a circular mobile phase front which transports the samples outwards in the respective circle segments.

It is likewise conceivable for a mobile phase storage container filled with mobile phase to be connected to the separating layer via a contact device. The contact device can be, for example, a capillary gap as described in DE 2818576 or preferably consist of a capillary-active material, for example a frit. The contact device can have, for example, a plate of a porous and capillary-active material which is mounted in a pivotable manner and projects with one end into the mobile phase storage container filled with mobile phase and whose other end can be pivoted out of a starting position into a development position, in which the contact device is connected to a side edge of the separating layer and continually wets the latter with the mobile phase. It is likewise conceivable for the contact device to consist of an L-shaped contact element whose first end is connected to the mobile phase storage container and whose second end may be connected to the separating layer along a side edge or may be disconnected from the separating layer. A comparatively large amount of the mobile phase can be applied to the separating layer via the contact device without major effort. In a preferred embodiment, the device according to the invention has a mobile phase storage container from which mobile phase can be brought into contact with the separating layer via a contact device. This mobile phase storage container is preferably filled with the aid of the autopipette. To this end, 100 µl and 5 ml of mobile phase, depending on the nature of the separating layer, are typically pipetted into the storage container from a further mobile phase storage container with the contact device. To this end, dispensing can be carried out once or multiple times. In this way, the start of thin-layer chromatography can, in addition, be determined and controlled by the pipetting of the mobile phase into the mobile phase storage container with contact device. As soon as the mobile phase is pipetted into the mobile phase storage container with contact device, it moves towards the separating layer through capillary forces, and the chromatographic separation of the sample begins.

In order to end the chromatographic separation, the contact device can be disconnected from the separating layer so that no further mobile phase can move into the separating layer. In addition or as an alternative, the mobile phase still located in the storage container can be removed therefrom by pipetting. In this way, the chromatographic separation can also be ended without removal of the contact device.

After ending of the chromatographic separation, i.e. after the development of the chromatogram, the mobile phase still located on the separating layer is typically at least partly removed, for example by evaporation. Apparatuses which are suitable for this purpose, such as, for example, heat lamps or fans, may be present in the device according to the invention. The evaluation of the chromatogram can be carried out by methods known to the person skilled in the art.

According to an advantageous embodiment of the inventive idea, it is provided, for the evaluation, that an eluent is taken up using a new pipette tip for each elution and brought into contact with an area of the separating layer to be evaluated, and that the eluate is fed to an evaluation device. In a preferred embodiment, an eluent having a sufficiently high water content is used if the separating layer is hydrophobic, so that the eluent is brought into contact with the separating layer using the pipette tip and dwells there as a drop. Due to the contact with the separating layer, sample substance from the separating layer is dissolved. After an exposure time of typically 1 to 10 seconds, the eluent with the sample dissolved therein is taken up by the pipette tip again and can be transported into an evaluation unit. The eluate can be fed, for example, to a mass spectrometer in order to facilitate extremely precise evaluation of the thin-layer chromatogram.

Alternatively, an area of the separating layer to be evaluated can be stamped out using a new pipette tip for each separation operation and fed to an evaluation device, for example a mass spectrometer.

In another embodiment, which, like the stamping out, is also suitable for hydrophobic and hydrophilic separating layers, a pipette tip, which is preferably provided with a cutting ring, is used to press through the sorbent layer and the cutting ring is used to seal off from the base support. A corresponding eluent is then added into the pipette tip, and the sorbent area delimited by the pipette tip is soaked with the eluent and eluted. A pipette tip with cutting ring is a pipette tip whose lower edge is of such a nature that it is stable and nevertheless sufficiently fine to be pressed through the sorbent layer of the separating layer onto the base support and to seal off there.

The embodiments mentioned above show that the extraction and feed of a sample of a thin-layer chromatogram to an evaluation device can also be carried out in this way with the aid of the autopipette. The separation and transfer of the sample necessary for the evaluation using one of the conventional analytical instruments can be carried out without significant time delay using the apparatus already used for the application and development of the sample.

In order to facilitate the quickest possible evaluation using external analytical equipment, it may be provided that a developed thin-layer chromatogram is evaluated exclusively by external analytical equipment and individual areas of the separating layer to be evaluated or individual eluates are fed successively to this analytical equipment. It is likewise conceivable for the separating layer to be scanned using optical analytical equipment, such as, for example, a UV lamp, and the optical information which can be obtained from the chromatogram to be evaluated. If treatment or processing of the chromatogram appears necessary or advantageous, corresponding method steps, for example chemical derivatisation, can be carried out before the optical evaluation.

The separating layer used for the development of the chromatogram can either be stored in an immobile manner in a suitable measuring device or moved or relocated within a housing of the device together with a support plate which accommodates and fixes the separating layer. For individual applications, it may be advantageous to swivel the separating layer or, for a treatment operation to be carried out manually, to detach the separating layer from the support plate or a suitable support-plate holder and to process it manually.

The invention also relates to a device for automated performance of thin-layer chromatography, having a support plate for the accommodation of a support layer, having a first storage container for the accommodation of a sample and having a second storage container for the accommodation of a mobile phase. The device preferably has further storage containers for the accommodation of samples, mobile phase or eluent. In accordance with the invention, it is furthermore provided that the device has a pipetting device which can be moved at least over one surface of the support plate and over the first storage container and the second storage container and has a stock of pipette tips, which can be taken up successively by the pipetting device, used and subsequently detached again and removed. Pipette tips are available commercially and inexpensively for various sample volumes and sample substances in various designs. Through the use of new pipette tips in each case for individual application or treatment operations, complex cleaning of an application unit can be avoided and it can at the same time be ensured that contamination of subsequent application operations or measurements by residues of a sample substance or a mobile phase used in the case of preceding application operations or measurements are excluded.

In an embodiment of the device according to the invention, the support plate is coolable and heatable. This enables the separating layer located on the support plate to be cooled during the development and thus for evaporation of the mobile phase to be reduced. Furthermore, heating can be carried out, for example after the development, in order to remove the mobile phase from the separating layer.

According to an advantageous embodiment of the inventive idea, it is provided that the support plate is arranged in a movable manner in a housing of the device. In order to shorten the time needed for application of a plurality of samples to a separating layer, and in order to shorten the subsequent development of the separating layer, it may be advantageous to move the support plate, together with the separating layer arranged on the support plate, relative to an automatically movable pipetting arm of an automatic pipetting device in order to shorten the individual movement distances of the pipetting device. It is likewise possible and, in view of rapid and reliable development of the chromatogram, advantageous to move the separating layer provided with samples and with a mobile phase into a substantially closed-off development container, at least during the development, and for this purpose the device may have an essentially closed development container which is suitable and designed for the accommodation of the support plate.

In order to be able to meet the various requirements for application of the sample and application of the mobile phase as rapidly and reliably as possible, it is provided in an embodiment that at least two different pipette tips are stored in the storage container for pipette tips. A first type of pipette tips may be designed for the application of individual, small amounts of a sample. A second type of pipette tips may have a larger accommodation volume and be suitable for the accommodation and application of the mobile phase to the separating layer.

It is preferably provided that the device has a storage container for an eluent. A further type of pipette tips which are used for taking up the eluent from the storage container for the eluent, for contacting an area of the separating layer to be evaluated with the eluent and for subsequent transfer of the eluate obtained here to an evaluation device may optionally be advantageous or necessary.

The evaluation necessary after the development of the thin-layer chromatogram can be accelerated by coupling an evaluation device to the device, so that individual eluate amounts or samples can be obtained from the separating layer and automatically fed to the evaluation device. The pipetting device can be used for transfer of the eluate or individual samples of the separating layer.

According to an embodiment of the inventive idea, it is provided that the device has pipette tips for the separation out of an area of the separating layer and for transfer of the separated-out area of the separating layer to an evaluation unit.

According to another embodiment of the inventive idea, it is provided that the device has pipette tips which are able to penetrate the sorbent layer and seal it off with the base support.

In a further embodiment, the device has a component for the removal of exhaust air. This can be, for example, an integrated fan or a connection port for an external fan or a suction device.

In another embodiment, the device according to the invention additionally has a storage container for separating layers. In a preferred variant of this embodiment, a separating layer can be removed automatically from the storage container and placed on the support plate.

In a further embodiment, the device according to the invention has a waste container for solvents into which residues of the mobile phase or samples can be pipetted. This waste container can be utilised, in the case of ending of the chromatographic separation, for the removal or disposal of the excess mobile phase from the storage container with contact device or in other pipetting operations for emptying the pipette tip before disposal thereof in the waste.

In a preferred embodiment, the device according to the invention has one or more mobile phase storage containers with a contact device. The contact device can be, for example, a capillary gap as described in DE 2818576 or preferably consist of a capillary-active material, for example a frit. Devices having two mobile phase storage containers with contact device offer the possibility of developing a separating layer in two directions. The mobile phase storage containers with contact device are preferably provided with a cooling device in order to prevent excessively fast evaporation of the mobile phase. Other storage containers may also optionally be coolable.

BRIEF DESCRIPTION OF THE DRAWINGS

The present invention is explained in greater detail below with reference to drawings, in which.

DETAILED DESCRIPTION OF THE PREFERRED EMBODIMENTS

Figure 1:
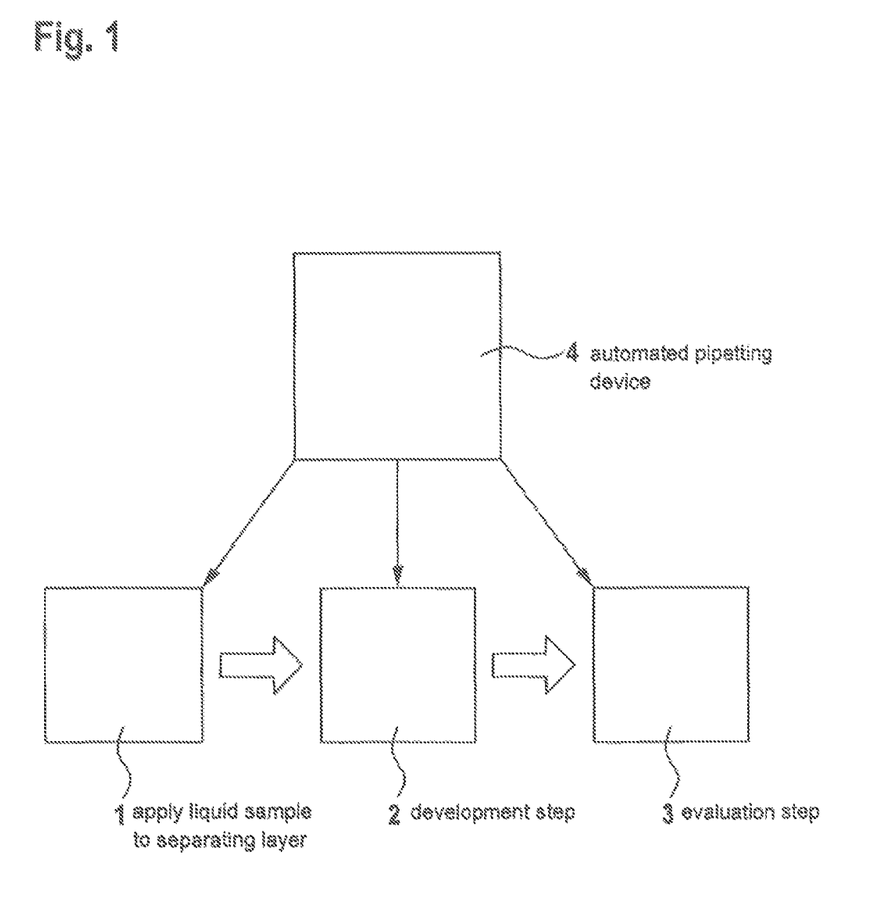
FIG. 1 shows a diagrammatic representation of a method sequence according to the invention for carrying out and evaluating thin-layer chromatography.

For the production and evaluation of thin-layer chromatography, which is depicted diagrammatically in FIG. 1, firstly, in a first method step 1, a liquid sample is applied to a separating layer having a suitable sorbent layer, such as, for example, silica gel. In a subsequent development step 2, a sufficient amount of a likewise liquid mobile phase is applied to a first area of the separating layer. Owing to capillary forces in the separating layer, the mobile phase moves on through the separating layer starting from the first area. In the process, the mobile phase entrains different components of the sample with different efficiencies during the movement along the separating layer caused by capillary forces. With increasing time, a spatial distribution of the individual components on the separating layer which is characteristic of the individual components is produced. In a subsequent evaluation step 3, a location-resolved evaluation and analysis of the individual components which have been spatially separated from one another during the development step 2 is carried out.

In accordance with the invention, it is provided that an automated pipetting device 4 is used at least for the application of the samples to the separating layer during the first method step 1. In order to avoid contamination of various samples or sample application operations to the separating layer, a new pipette tip are connected to the pipetting device 4 on each change of the samples or even for each pipetting operation.

The automated pipetting device 4 is advantageously also used immediately before and during the development step 2 for the application of the mobile phase to the separating layer or in the storage container with contact device and during the evaluation step 3 for the direct transfer of the location-resolved sample amounts to a separate evaluation device.

Figure 2:
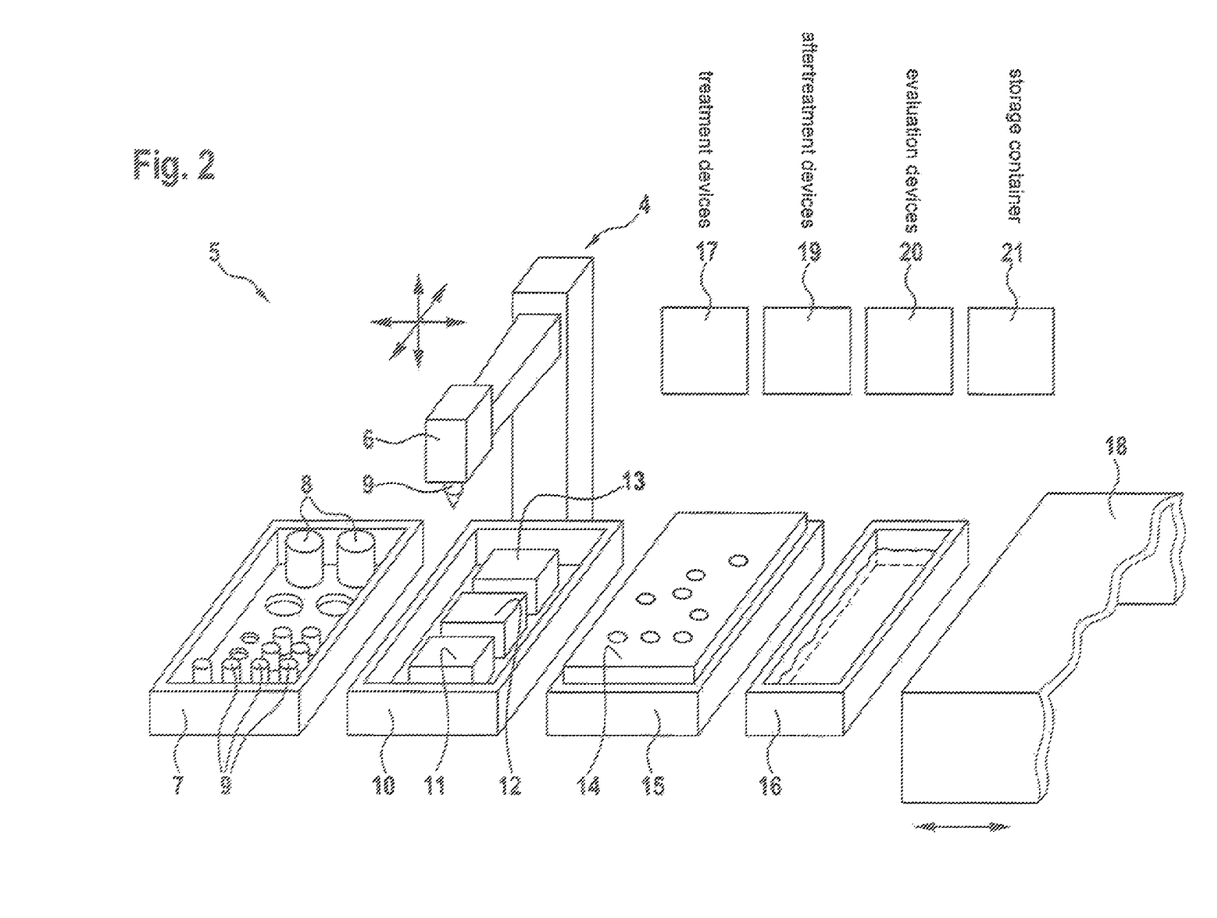
FIG. 2 shows an illustrative view of a device for carrying out the method according to the invention and FIG. 3 shows a diagrammatic sectional view of a device for the automated application of a mobile phase to a separating layer to which a plurality of samples have already been applied.

FIG. 2 depicts by way of example and in a simplified manner for illustration an illustrative embodiment of a fully automated device 5 for carrying out thin-layer chromatography. The automated pipetting device 4 has a pipetting head 6 which can be moved in all three spatial directions. The pipetting head 6 is able to grasp in each case a single pipette tip 8, 9 from a pipette tip storage container 7 and use it for subsequent pipetting operations. Various pipette tips 8, 9 which differ in shape and capacity are stored in the pipette tip storage container 7, so that a pipette tip 8, 9 which is in each case matched to the requirements can be selected and used for various application operations.

In a first container 10 arranged adjacently, various samples 11, 12, 13 are arranged. The pipetting device 4 is able to take up a small amount of the sample 11 using the selected pipette tip 9 and apply it to a separating layer 14 which is fixed on a support plate 15. The separating layer 14 has a layer thickness of, for example, 200 µm, where smaller layer thicknesses are also advantageous and possible. The separating layer 14 has, for example, dimensions of about 10 cm×5 cm. Here too, smaller dimensions of, for example, 6 cm×4 cm are conceivable. In order to be less sensitive in the positioning and application of the small amount of the sample 11 to the separating layer 14, it is advantageous if the separating layer 14 has a concentration zone, which is not depicted in FIG. 2.

For subsequent application steps of the further samples 12 and 13, firstly the pipette tip 9 already used is disposed of, and a new pipette tip 8 or 9 is grasped in order subsequently to apply the amounts prespecified in each case of the further samples 12 and 13 likewise to the separating layer 14. The use of new pipette tips 8, 9 in each case excludes contamination of subsequent application operations by residues of preceding application operations unintentionally remaining. Interim cleaning of the automated device 5 or the pipetting device 4 is not necessary.

A mobile phase is subsequently taken up from a second storage container 16, likewise using a new pipette tip 8, and applied to the separating layer 14. The development of the thin-layer chromatogram can be influenced by various treatment devices 17, which are merely indicated diagrammatically. A cover 18 can be pushed over the separating layer 14 from the side in order to reduce impairment of the separating layer 14 and the thin-layer chromatogram by external influences during the development step 2. At the same time, the development can be accelerated or advantageously influenced in another manner by suitable treatment devices 17, which may be integrated into the cover 18. The cover 18 forms an essentially closed development container in conjunction with surrounding housing regions.

After completion of the development step 2, the thin-layer chromatogram can be treated using further aftertreatment devices 19 in order to simplify the evaluation and enable it to become reproducible. The aftertreatment devices 19, which are likewise only indicated diagrammatically, may contain, for example, a heat source or an infrared light source. Further reagents could optionally also be applied using the pipetting device 4. A spray device, by means of which, for example, a ninhydrin treatment of the separating layer can be carried out, is also possible.

Finally, the thin-layer chromatogram produced can be evaluated using separate evaluation devices 20. The evaluation devices 20 may include optical analysis equipment, such as, for example, lamps, preferably UV lamps, and/or scanner devices. It is likewise conceivable for individual areas of the separating layer 14 to be separated out using a separate pipette tip 8, 9 and transferred to a mass spectrometer. It is likewise possible to take up an eluent from a storage container 21, which is only indicated diagrammatically, using the pipetting device 4, to bring it into contact with the separating layer 14 at a prespecified position, and to transfer the eluate obtained to an evaluation device 20, for example a mass spectrometer.

Figure 3:
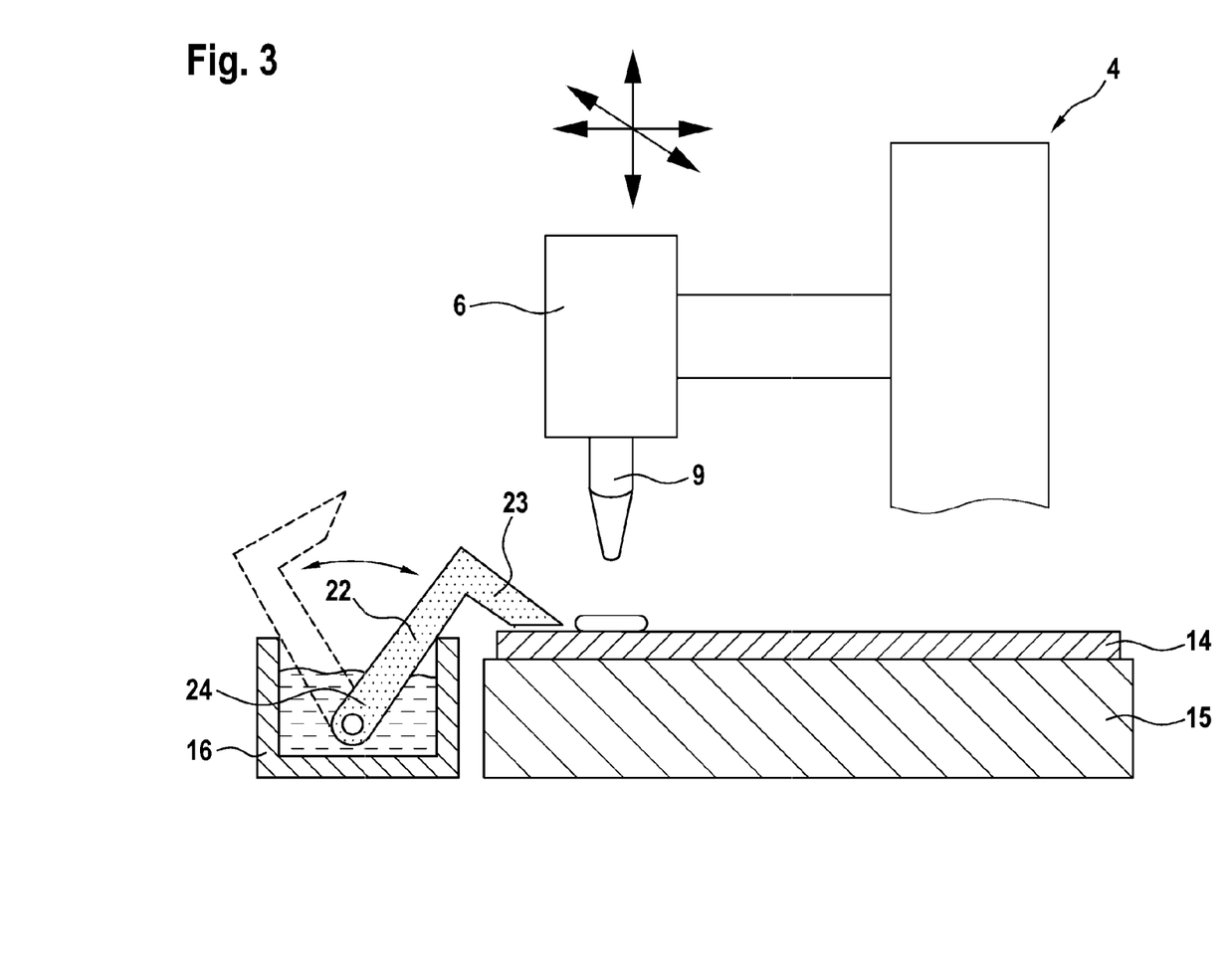

FIG. 3 depicts by way of example a contact device 22 for the application of the mobile phase to the separating layer 14. The angular contact device 22 is mounted in a pivotable manner and can be moved to and fro between a contact position, in which an angled-off end region 23 of the contact device 22 is in contact with the separating layer 14, and a starting position, depicted by dashed lines. The contact device 22 consists of a porous and capillary-active material. A second end region 24 is mounted in a pivotable manner in the second storage container 16, so that mobile phase is conveyed continuously out of the second storage container 16 into the angled-off end region 23 owing to capillary forces. When or as long as the contact device 22 is in the contact position, the mobile phase is transported via the angled-off end region 23 onto the separating layer 14. The contact device 22 may of course also have a shape or position deviating from the illustrative embodiment depicted by way of example.

The present invention thus provides a method and device for the automatic and reliable performance of thin-layer chromatographic separations. It has been found that the use of exchangeable pipette tips allows sufficiently accurate application of the reagents and at the same time is ideally suitable for avoiding contamination. The autopipette of the device according to the invention can preferably be employed not only for sample application, but also for the introduction or application of the mobile phase and eluent. It has furthermore been found that the method according to the invention and the device according to the invention are particularly suitable for carrying out separations on small separating layers of small diameter. Preference is given to separating layers whose longest dimension is 10 cm or less, preferably between 5 and 8 cm. These separating layers preferably have a sorbent layer having thicknesses below 200 µm, preferably between 10 and 100 µm. In a further preferred embodiment, the separating layers have a concentration zone.

Even without further comments, it will be assumed that a person skilled in the art will be able to utilise the above description in the broadest scope. The preferred embodiments and examples should therefore merely be regarded as descriptive disclosure which is absolutely not limiting in any way.

The complete disclosure content of all applications, patents and publications mentioned above and below, in particular the corresponding application EP 12008479.3, filed on 20 Dec. 2012, is incorporated into this application by way of reference.

EXAMPLE

Description for Carrying out Fully Automatic Thin-Layer Chromatography

The example describes the performance of fully automatic thin-layer chromatography using the NanoMate® system (Advion) and a horizontal chamber for 5×5 cm plate format (Desaga). The NanoMate® system is a pipetting system combined with a nano spray source for coupling to mass spectrometry. The horizontal chamber is integrated into the NanoMate® system by means of a specially made adapter part. In addition to the horizontal chamber, the adapter part also contains a plurality of reservoirs which can be used for introduction of the sample or solvents.

Sample Application:

The plate is placed in the support of the horizontal chamber with the layer facing upwards and the sample is introduced into one of the reservoirs. The instrument is programmed so that the sample is taken up using a fresh pipette tip and pipetted onto the corresponding positions on the plate.

Chromatogram Development:

The solvents necessary for the mobile phase are introduced into reservoirs. The instrument is programmed so that the corresponding amounts of solvent are always taken up using fresh pipette tips and combined and mixed in a free reservoir. After the mixing, the instrument takes up the requisite amount of mobile phase and dispenses it into the mobile phase container of the horizontal chamber. The mobile phase is automatically sucked up via the frit by means of capillary forces and transported into the separating layer through contact with the plate material, causing the chromatogram development to begin automatically. The chromatogram development is ended through the mobile phase being consumed or the instrument pipetting the remainder out of the mobile phase container.

Sample Extraction by LESA® (Liquid Extraction Surface Analysis)

The coupling to mass spectrometry is carried out via the LESA® mode of the system. To this end, the original holder from the manufacturer is installed in the instrument, and the plate is clamped in with the layer facing upwards. The conversion is necessary since the software for the LESA® mode is calibrated to the original holder. The corresponding eluent is introduced into a reservoir or mixed in the instrument analogously to the mobile phase preparation. The instrument is programmed so that one drop of the eluent is brought into contact with the substance zone and the sample solution obtained in this way is fed automatically into the mass spectrometer via the nano spray source.

The invention claimed is:

1. A method for performing thin-layer chromatography, the method comprising:
   applying at least one liquid sample to a separating layer (14), wherein the separating layer is positioned on a horizontal support plate,
   subsequently applying a mobile phase to the separating layer (14) positioned on the horizontal support plate and bringing the mobile phase into contact with the sample, and
   after a development phase, producing a thin-layer chromatogram wherein the liquid sample is taken up from a sample storage container (11, 12, 13) with the aid of an autopipette (4) using a new pipette tip (8, 9) for each sample application operation and applied to the separating layer (14),
   wherein an area of the separating layer to be evaluated is stamped out using the new pipette tip for each separation operation and fed to an evaluation device.

2. The method according to claim 1, wherein the mobile phase is taken up from a mobile phase storage container (16) using the new pipette tip (8, 9) for each mobile phase application operation and applied to the separating layer (14).

3. The method according to claim 1, wherein a mobile phase storage container (16) filled with mobile phase is connected to the separating layer (14) via a contact device (22) comprising a capillary-active material.

4. The method according to claim 1, wherein an eluent is taken up using the new pipette tip (8, 9) for each elution and brought into contact with an area of the separating layer (14) to be evaluated, and further wherein the eluate is fed to an evaluation device (20).

5. The method according to claim 1, wherein an area of the separating layer (14) to be evaluated is sealed off as far as the base support using the new pipette tip (8, 9) for each elution, wherein a sorbent located in the sealed-off area is brought into contact with an eluent, and the eluate formed is fed to an evaluation device (20).

6. A device (5) for performing thin-layer chromatography automatically, the device comprising:
   a horizontal support plate (15) for the accommodation of a separating layer (14),
   a first storage container (10, 11, 12, 13) for the accommodation of a sample, and
   a second storage container (16) for the accommodation of a mobile phase,
   wherein the device (5) has an automatic pipetting device (4) which is moved at least over one surface of the horizontal support plate (15) and over the first storage container (10, 11, 12, 13) and the second storage container (16) and has a stock of pipette tips (8, 9), which is taken up successively by the pipetting device (4), used and subsequently detached from the pipetting device (4) again and removed, and
   wherein the horizontal support plate is held in a horizontal position during the mobile phase,
   wherein the device has the pipette tips for separating out an area of the separating layer and for transfer of the separated-out area of the separating layer to an evaluation unit.

7. The device (5) according to claim 6, wherein characterised the horizontal support plate (15) is arranged in a movable manner in a housing of the device (5).

8. The device (5) according to claim 6, wherein the horizontal support plate (15) is connected to the storage container (16) for the mobile phase via a contact device (22) comprising a capillary-active material.

9. The device (5) according to claim 6, wherein the device (5) has an essentially closed development container for the accommodation of the horizontal support plate (15).

10. The device (5) according to claim 6, wherein at least two different types of the pipette tips (8, 9) are stored in a third storage container (7) for the pipette tips (8, 9).

11. The device (5) according to claim 6, wherein the device (5) has a storage container (21) for an eluent.

12. The device (5) according to claim 6, wherein the device (5) has the pipette tips (8, 9) for sealing off a sorbent area of the separating layer (14) and for elution of the sealed-off sorbent area and transfer of the eluate to an evaluation unit (20).

* * * * *